United States Patent [19]

Van Keulen et al.

[11] Patent Number: 5,348,956
[45] Date of Patent: Sep. 20, 1994

[54] SUBSTITUTED CYCLOPROPYLAMINO-1,3,5-TRIAZINES

[75] Inventors: Berend J. Van Keulen, Tubize, Belgium; Solo Goldstein, Montreal, Canada; Eric Cossement, Bruxelles, Belgium; Jean Gobert, Bruxelles, Belgium; Ernst Wülfert, Bruxelles, Belgium

[73] Assignee: UCB S.A., Bruxelles, Belgium

[21] Appl. No.: 103,119

[22] Filed: Aug. 9, 1993

Related U.S. Application Data

[62] Division of Ser. No. 914,583, Jul. 20, 1992, Pat. No. 5,258,513.

[30] Foreign Application Priority Data

Jul. 25, 1991 [GB] United Kingdom ................ 9116039

[51] Int. Cl.$^5$ .................... A61K 31/535; A61K 31/53
[52] U.S. Cl. ............................ 514/232.2; 514/232.8; 514/236.2; 514/245; 514/826; 514/886
[58] Field of Search ............... 514/232.2, 232.8, 236.2, 514/245, 208, 241, 826, 886; 544/197, 198

[56] References Cited

U.S. PATENT DOCUMENTS 4,160,831 7/1979 Laanio et al. ................ 514/236.2
4,260,753 4/1981 Berrer et al. ................ 544/208
4,956,363 9/1990 Wülfert et al. ................ 514/236.2
4,956,367 9/1990 Cossement ................ 514/236.2

Primary Examiner—Marianne M. Cintins
Assistant Examiner—K. Weddington
Attorney, Agent, or Firm—Wenderoth, Lind & Ponack

[57] ABSTRACT

New substituted cyclopropylamino-1,3,5-triazines having the formula

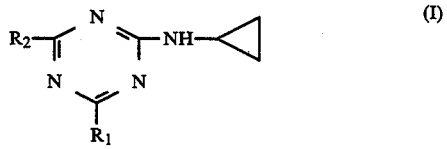

wherein
$R_1$ is $C_1$-$C_3$-alkyl, $C_3$-$C_5$-cycloalkyl or $C_1$-$C_3$-alkyl-$C_3$-$C_5$-cycloalkyl
$R_2$ is bis(2-hydroxyethyl)amino, 3-hydroxy-1-azetidinyl, 3-methoxy-1-azetidinyl, 3-oxo-1-azetidinyl, morpholino, 4-hydroxypiperidino, thiomorpholino, thiomorpholino S-oxide, thiomorpholino S,S-dioxide, 3-thiazolidinyl, 3-thiazolidinyl S-oxide, 3-thiazolidinyl S,S-dioxide or 8-oxa-3-azabicyclo[3,2,1]oct-3-yl. Processes for the preparation thereof and pharmaceutical composition containing them are also given. The compounds are useful for the treatment of inflammation and asthma.

7 Claims, No Drawings

SUBSTITUTED CYCLOPROPYLAMINO-1,3,5-TRIAZINES

This is a divisional application of Ser. No. 07/914,583, filed Jul. 20, 1992; U.S. Pat. No. 5,258,513.

The present invention relates to new substituted cyclopropylamino-1,3,5-triazines and the non-toxic, pharmaceutically acceptable acid addition salts thereof, as well as to processes for the preparation thereof and to the therapeutic use thereof. It also relates to pharmaceutical compositions containing these new compounds.

2-trifluoromethyl-1,3,5-triazines which are substituted in the 4-position, inter alia, by an alkyl, substituted or unsubstituted alkylamino, dialkylamino, cycloalkylamino, morpholino or 4-alkyl-1-piperazinyl radical, and in the 6-position by the same radicals, except the alkyl radical, are already known from Japanese Patent Application No. 25786/78. According to this patent application, these compounds have tranquilizing and anticonvulsive properties.

Moreover, British Patent No. 1,053,113 describes 1,2-dihydro-1-hydroxy-1,3,5-triazines which are substituted in the 2-position by an imino radical, optionally substituted by an alkyl, alkenyl, cycloalkyl, phenyl or naphthyl (optionally substituted by an alkyl radical) radical, in the 4-position by a dialkylamino, dialkenylamino, N-alkylalkenylamino, aziridinyl, azetidinyl, pyrrolidinyl, piperidino, hexahydroazepinyl, heptamethyleneimino, octamethyleneimino or morpholino radical, each of said heterocyclic radicals being possibly substituted by 1 to 3 alkyl radicals, and in the 6-position by a hydrogen atom or an alkyl, alkenyl, alkoxyalkyl, cycloalkyl, phenyl or naphthyl radical, optionally substituted by an alkyl, aralkyl, alkylaralkyl, alkoxyaralkyl or haloaralkyl radical. According to this patent, these compounds are antihypertensive agents which can be used for the treatment of hypertension and shock states; they are also described as secretion inhibitors and central nervous system depressants. These compounds are prepared by oxidation of the corresponding 1,3,5-triazines carrying the same substituents in the 2-, 4- and 6-positions. However, there is no suggestion in this patent that the intermediate 1,3,5-triazines could have any pharmacological activity. Moreover, this patent does not describe any 1,3,5-triazine substituted by a cyclopropylamino radical.

Finally, U.S. Pat. No. 4,956,367 (assigned to the assignee of the present invention) describes 2-amino-4-morpholino-6-propyl-1,3,5-triazines in which the amino group in the 2-position is substituted by different radicals such as, for example, a hydroxyl group or a hydroxyalkyl radical. These compounds can be used for the treatment of cognitive and behavioral disorders associated with ageing and with dementia syndromes, for example, those associated with Alzheimer's disease. However, this patent does not describe 1,3,5-triazines substituted by a cyclopropylamino radical.

Continuing its research work in this field, applicant has now found new cyclopropylamino substituted 1,3,5-triazines which have valuable pharmaceutical properties and, in particular, the property to promote learning and to attenuate the amnesic effect resulting from cholinergic hypofunctioning induced by a cholinergic antagonist such as, for example, scopolamine. The cholinergic system is widely involved in the phenomena of memorization and learning. Thus, for example, administration of an anticholinergic agent such as scopolamine to young subjects gives rise to memory deficiencies similar to those observed in elderly subjects. Conversely, cholinergic agents, such as physostigmine, are capable of combating the amnesia resulting from the administration of anticholinergic agents (S. D. GLICK et al., Behavioral Biology, 7, (1972), 245–254; U. SCHINDLER et al., Drug Develop. Res., 4, (1984), 567–576). For this reason, the compounds according to the invention can be used for the treatment of cognitive and behavioral disorders associated with ageing and with dementia syndromes. In particular, they are used in the treatment of disorders associated with Alzheimer's disease, with senile dementia, Alzheimer's type and with any evolutive cognitive pathology (C. G. GOTTFRIES, Psychopharmacology, 86, (1985), 245–252; C. G. GOTTFRIES, Neurobiology of Ageing, 4, (1983), 261–271).

The compounds according to the present invention also have a central serotonergic activity, demonstrated by the power which they have to induce a particular stereotypy in rats usually known as "Wet Dog Shake" (A. R. GREEN and D. J. HEAL in "Neuropharmacology of Serotonin", Ed. A. R. GREEN, Oxford Univ. Press, 1985, Chapter 12, pages 326 to 365). It is known that serotonin plays an important role in the regulation of the neuroendocrine function, which may be disturbed in pathologies such as depression, anxiety and mood disturbances. A decrease in serotonergic activity is associated with numerous changes in mood and somatic functions occurring in depressed patients (H. Y. MELTZER and M. T. LOWY in "Psychopharmacology: The Third Generation of Progress", Ed. H. Y. MELTZER, Raven Press, New York, 1987, Chapter 52, pages 513 to 520). The compounds according to the invention can thus be used for the treatment of these various pathologies associated with a slowing down in serotonergic activity.

In addition, at the peripheral level, the compounds according to the invention also have a bronchospamolytic activity and an inhibiting activity on the release of mastocyte mediators during an anaphylactic aggression. The compounds according to the invention moreover potentiate the muscle-relaxing effect of a β-adrenergic agonist (for example isoprenaline) on a smooth muscle contracted by histamine, and also have an anti-inflammatory and anti-edema activity. For this reason, the compounds according to the invention can also be used in the treatment of inflammatory phenomena and asthma, in particular as an alternative to treatment with theophylline or even with bronchodilatory agents such as β-sympathomimetic agents, which are known to cause, during prolonged administration, desensitization of the β-adrenergic receptors in the bronchi, to the extent of rendering the bronchospasm of chronic asthmatics insensitive and irreversible to the action of these agents. More particularly, the present invention relates to new substituted cyclopropylamino-1,3,5-triazines having the general formula

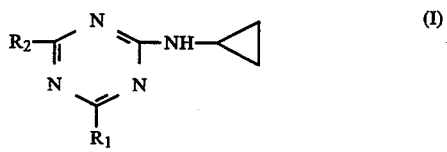

wherein $R_1$ represents an alkyl radical, an unsubstituted cycloalkyl radical or a cycloalkyl radical substituted by at least one alkyl radical, preferably by one or two alkyl radicals, the alkyl radicals having 1 to 3 carbon atoms and the cycloalkyl radicals having 3 to 5 carbon atoms, and $R_2$ represents a bis(2-hydroxyethyl)amino, 3-hydroxy-1-azetidinyl, 3-methoxy-1-azetidinyl, 3-oxo-1-azetidinyl, morpholino, 4-hydroxypiperidino, thiomorpholino, thiomorpholino S-oxide, thiomorpholino S,S-dioxide, 3-thiazolidinyl, 3-thiazolidinyl S-oxide, 3-thiazolidinyl S,S-dioxide or 8-oxa-3-azabicyclo[3,2,1]oct-3-yl radical, and to the non-toxic pharmaceutically acceptable acid addition salts thereof.

The preferred compounds according to the present invention are the cyclopropylamino-1,3,5-triazines of general formula I wherein $R_2$ represents a morpholino, thiomorpholino or thiomorpholino S,S-dioxide radical, and the non-toxic pharmaceutically acceptable acid addition salts thereof.

Particularly preferred compounds according to the invention include:

2-cyclopropylamino-4-morpholino-6-n-propyl-1,3,5-triazine, 2-cyclopropyl-4-cyclopropylamino-6-morpholino-1,3,5-triazine hydrochloride, 2-cyclobutyl-4-cyclopropylamino-6-morpholino-1,3,5-triazine, 2-cyclopropyl-4-cyclopropylamino-6-thiomorpholino-1,3,5-triazine, and 2-cyclopropyl-4-cyclopropylamino-6-thiomorpholino-1,3,5-triazine S,S-dioxide.

The present invention also relates to the non-toxic pharmaceutically acceptable acid addition salts of the substituted cyclopropylamino-1,3,5-triazines of formula I. As examples of pharmaceutically acceptable acids there may be mentioned mineral acids, such as hydrochloric, hydrobromic, sulfuric, nitric and phosphoric acid and organic acids, such as acetic, citric, tartaric, benzoic, salicylic and maleic acid.

When the molecule contains one or more asymmetric carbon atoms, the compounds of formula I may be either in the form of a racemic mixture or in the form of one of the enantiomers. These various forms are also within the scope of the present invention.

The substituted cyclopropylamino-1,3,5-triazines according to the present invention can be prepared by one of the following processes:

(a) A chloro-cyclopropylamino-1,3,5-triazine of the formula II is reacted with an amine of the formula $R_2H$ (III) according to the equation

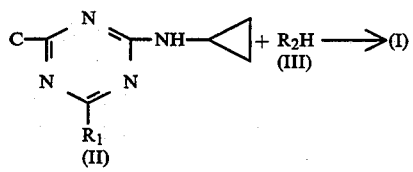

In these formulae, $R_1$ and $R_2$ have the meanings given above.

(b) A chloro-1,3,5-triazine of the formula IV is reacted with cyclopropylamine of the formula V according to the equation

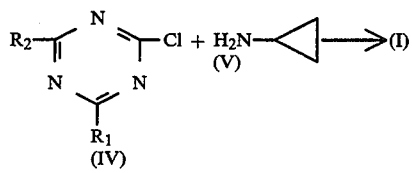

In these formulae, $R_1$ and $R_2$ have the meanings given above.

(c) An N-cyclopropylbiguanide of the formula VI is reacted with an alkyl ester of the formula VII by heating under reflux for several hours in an aliphatic alcohol in the presence of an alkali metal alcoholate according to the equation

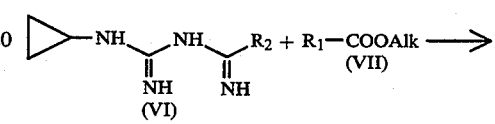

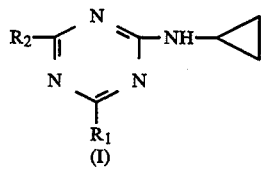

In these formulae, $R_1$ and $R_2$ have the meanings given above and Alk represents an alkyl radical having 1 to 4 carbon atoms, preferably the ethyl radical.

(d) A cyclopropylamino-1,3,5-triazine of the formula I, wherein $R_1$ has the meaning given above and $R_2$ represents a thiomorpholino or 3-thiazolidinyl radical, is oxidized in order to prepare the cyclopropylamino-1,3,5-triazines of the formula I, wherein R represents a thiomorpholino S-oxide, thiomorpholino S,S-dioxide, 3-thiazolidinyl S-oxide or 3-thiazolidinyl S,S-dioxide radical.

Processes (a) and (b) above are carried out by heating at elevated temperature for several hours in an inert solvent, preferably dioxane or isopropyl alcohol; in general, they are carried out by heating at the boiling point of the solvent used and in the presence of a base. The base, which is used to neutralize the hydrochloric acid liberated in the course of the reaction, can be either the amine which itself is used in the reaction or another organic base (for example triethylamine) or an inorganic base (for example potassium carbonate).

The starting compounds of the formula II are prepared by conventional methods, by reacting a 2,4-dichloro-6-$R_1$-1,3,5-triazine of the formula VIII with cyclopropylamine of the formula V according to the equation

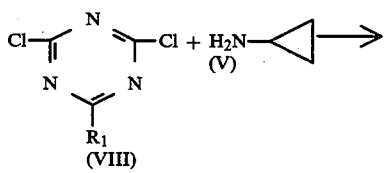

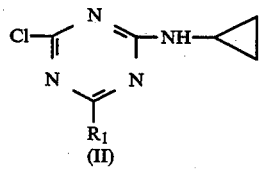

In these formulae, R₁ has the meaning given above.

This reaction is generally carried out at a temperature between −10° C. and room temperature in an inert solvent, such as chloroform, and in the presence of an inorganic or organic base, such as, for example, potassium carbonate, to neutralize the hydrochloric acid liberated during the reaction.

The starting compounds of the formula IV are also prepared by conventional methods, by reacting a 2,4-dichloro-6-R₁-1,3,5-triazine of the formula VIII with an amine of the formula R₂H (III) according to the equation

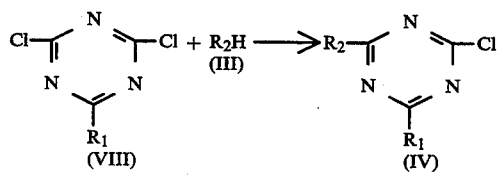

In these formulae, R₁ and R₂ have the meanings given above.

This reaction is generally carried out at a temperature between 0° C. and 20° C., in an inert solvent, such as chloroform, and in the presence of a base, for example potassium carbonate.

The 2,4-dichloro-6-R₁-1,3,5-triazines of the formula VIII used as starting compounds can be prepared by the process of R. HIRT et al. (Helv. Chim. Acta, 33, (1950), 1365–1369), which comprises reacting cyanuric chloride with a suitable organomagnesium compound of the formula R₁MgX, wherein R₁ has the meaning given above and X represents a halogen atom, preferably an iodine or bromine atom.

The starting compounds of the formula VI, used in process (c), are prepared by a two-step process:

(1) reacting cyclopropylamine of the formula V with the sodium salt of cyanoguanidine of the formula IX to obtain the N-cyano-N′-cyclopropylguanidine of the formula X according to the equation

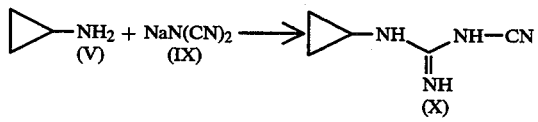

(2) heating N-cyano-N′-cyclopropylguanidine of the formula X with an amine of the formula R₂H (III) at a temperature of about 160° C. for several hours under an inert atmosphere to obtain the N-cyclopropylbiguanide of the formula VI according to the equation

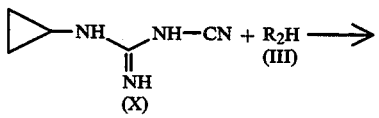

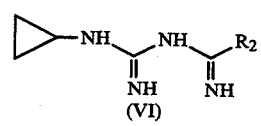

In these formulae, R₂ has the meaning given above.

As far as process (d) is concerned, wherein a cyclopropylamino-1,3,5-triazine of the formula I substituted by a thiomorpholino or 3-thiazolidinyl radical and prepared according to one of the processes (a), (b) or (c), is oxidized, this process results in the formation of the corresponding S-oxide or S,S-dioxide derivative according to the conditions of operation used to carry out the oxidation. This oxidation is generally carried out by means of potassium peroxomonosulfate (commercialized under the name oxone, 2 KHSO₅.KHSO₄.K₂SO₄). The S,S-dioxide derivative is obtained when the reaction is carried out at a temperature between 10° and 20° C. and in the presence of 1 to 2 moles of oxone per mole of the compound of formula I to be oxidized. On the contrary, the S-oxide derivative is obtained when the reaction temperature is maintained between −5° C. and +5° C. and only about 0.5 mole of oxone per mole of the compound of formula I is used.

The non-toxic pharmaceutically acceptable acid addition salts can be prepared from the substituted cyclopropylamino-1,3,5-triazines of the formula I by methods which are known per se.

The following examples illustrate the present invention without limiting it.

EXAMPLE 1

Preparation of the starting 2,4-dichloro-6-R₁-1,3,5-triazines of the formula VIII.

2,4-Dichloro-6-ethyl-1,3,5-triazine.

1.5 equivalent of ethylmagnesium bromide dissolved in diethyl ether (prepared by reacting magnesium with ethyl bromide) are added dropwise to a suspension of one equivalent of cyanuric chloride in toluene, while keeping the temperature of the reaction mixture between 10° and 15° C. After the addition, this mixture is kept at room temperature for one hour. An aqueous solution containing 1.5 equivalent of hydrochloric acid is then added. The two phases are separated, the organic phase is dried over sodium sulfate, then the solvent is removed under reduced pressure. 2,4-dichloro-6-ethyl-1,3,5-triazine is purified by distillation under reduced pressure. Yield: 63%. B.P.: 83° C./17 mbars.

The compounds summarized in Table I are prepared in the same manner.

TABLE I 2,4-dichloro-6-R₁-1,3,5-triazines

| R₁ | Solvent (1) | Solvent (2) | B.P. °C./mbars | Yield (in %) |
| --- | --- | --- | --- | --- |
| methyl (3) | Et₂O | toluene | 80–82/16 | 40 |
| n-propyl | Et₂O | toluene | 110/25 | 60 |
| isopropyl | Et₂O | toluene | 87/20 | 29 |
| cyclopropyl | Et₂O | benzene | — (4) | — |
| cyclobutyl | THF | toluene | — (4) | — |

TABLE I-continued

| | 2,4-dichloro-6-$R_1$-1,3,5-triazines | | | |
|---|---|---|---|---|
| $R_1$ | Solvent (1) | Solvent (2) | B.P. °C./mbars | Yield (in %) |
| cyclopentyl | $Et_2O$ | benzene | 135/13 | 25 |

$Et_2O$: diethyl ether; THF: tetrahydrofuran.
(1): solvent used to prepare the organomagnesium compound,
(2): aromatic solvent used for the dispersion of cyanuric chloride,
(3): organomagnesium compound prepared from methyl iodide,
(4): the reaction product is not isolated by distillation: after addition of the organomagnesium compound, the reaction mixture is concentrated and the residue is taken up in anhydrous diethyl ether. The mixture is filtered on neutral Dicalite, the filtrate is evaporated and the residue is used as such in the following step.

EXAMPLE 2

Preparation of the cyclopropylamino-1,3,5-triazines of the formula I according to process (a).

A. Preparation of the starting chloro-cyclopropylamino-1,3,5-triazines of the formula II.

2-Chloro-4-cyclopropylamino-6-methyl-1,3,5-triazine (new compound). 1 mole of cyclopropylamine dissolved in chloroform is added to a molar solution of 2,4-dichloro-6-methyl-1,3,5-triazine in chloroform, previously cooled to $-10°$ C. After the addition, the mixture is allowed to return to room temperature. The mixture is then cooled again to about 0° C. and an aqueous solution containing 1 mole of potassium carbonate is added. Stirring is continued for 1 to 2 hours at room temperature. The organic phase is separated off and dried over sodium sulfate, and the solvent is evaporated under reduced pressure. The residue is recrystallized from hexane. 2-Chloro-4-cyclopropyl-amino-6-methyl-1,3,5-triazine is thus obtained. Yield: 75%. M.P.: 117°-119° C.

The following new compounds are prepared in the same manner: 2-Chloro-4-cyclopropylamino-6-ethyl-1,3,5-triazine.

The residue obtained after evaporation of the solvent (crude yield: 100%) is used as such in the following step.

2-Chloro-4-cyclopropylamino-6-n-propyl-1,3,5-triazine. Yield: 100%. B.P.: 125°/0.4 mbar.

2-Chloro-4-cyclopropylamino-6-isopropyl-1,3,5-triazine. This compound is recrystallized from hexane. Yield: 74%. M.P.: 79°-80° C.

2-Chloro-4-cyclopropyl-6-cyclopropylamino-1,3,5-triazine. This compound is recrystallized from hexane. Yield (calculated on the basis of cyanuric chloride): 71.5%. M.P.: 66°-67° C. 2-Chloro-4-cyclobutyl-6-cyclopropylamino-1,3,5-triazine. Crude yield (calculated on the basis of the cyanuric chloride): 23%. The product is used as such, without other purification, in the following step.

2-Chloro-4-cyclopentyl-6-cyclopropylamino-1,3,5-triazine. Yield (crude): 100%. The crude product is used as such in the following step.

B. Preparation of the cyclopropylamino-1,3,5-triazines of the formula I.

1. 2-Cyclopropylamino-4-morpholino-6-n-propyl-1,3,5-triazine (compound 1). 45 ml (0.45 mole) of morpholine dissolved in 200 ml of dioxane are added to a solution containing 43 g (0.163 mole) of 2-chloro-4-cyclopropylamino-6-n-propyl-1,3,5-triazine in 300 ml of dioxane, while maintaining the mixture at room temperature. After the addition, the mixture is heated under reflux for one to two hours. The reaction mixture is then allowed to return to room temperature and the precipitate is filtered off. The filtrate is concentrated and the residue is redissolved in dichloromethane. The solution is washed with water. The organic phase is separated off and dried over sodium sulfate. The solvent is evaporated under reduced pressure. The residue is purified by chromatography on silica (eluent: 98.5:1.5 (v/v) dichloromethane-ethanol) and the product is finally recrystallized from diethyl ether. 36.2 g of 2-cyclopropylamino-4-morpholino-6-n-propyl-1,3,5-triazine are obtained.

Yield: 85%. M.P.: 104° C. Analysis for $C_{13}H_{21}N_5O$ in %: calc.: C 59.29 H 8.04 N 26.59 found: 59.20 8.15 26.43.

The compounds summarized in Table II are prepared in the same manner.

TABLE II

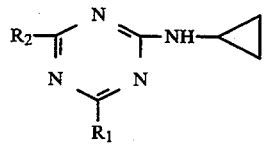

| Compound | $R_1$ | $R_2$ | Yield (%) | M.P. (°C.) | | calc. % | found % |
|---|---|---|---|---|---|---|---|
| | | | | | | | Analyses |
| 2 | ethyl | morpholino | 61 | 152(1) | C | 50.44 | 50.00 |
| | | | | | H | 7.05 | 7.06 |
| | | | | | N | 24.51 | 24.10 |
| | | | | | $Cl^-$ | 12.40 | 12.50 |
| 3 | cyclopropyl | morpholino | 67.4 | 183(1) | C | 52.44 | 52.77 |
| | | | | | H | 6.72 | 6.80 |
| | | | | | N | 23.53 | 22.16 |
| | | | | | $Cl^-$ | 11.93 | 11.92 |
| 4 | cyclobutyl | morpholino | 80.7 | 119 | C | 61.09 | 61.68 |
| | | | | | H | 7.64 | 7.67 |
| | | | | | N | 25.82 | 25.35 |
| 5 | n-propyl | 4-hydroxy-piperidino | 63.9 | 102 | C | 60.65 | 60.98 |
| | | | | | H | 8.30 | 8.46 |
| | | | | | N | 25.27 | 24.04 |
| 6 | n-propyl | $N(CH_2CH_2OH)_2$ | 68 | 124(1) | C | 49.13 | 49.54 |
| | | | | | H | 7.56 | 7.48 |
| | | | | | N | 22.05 | 22.85 |
| | | | | | $Cl^-$ | 11.18 | 11.18 |
| 7 | cyclopropyl | $N(CH_2CH_2OH)_2$ | 30.8 | 94 | C | 55.91 | 55.90 |
| | | | | | H | 7.53 | 7.53 |

| Compound | R₁ | R₂ | Yield (%) | M.P. (°C.) | | calc. % | found % |
|---|---|---|---|---|---|---|---|
| | | | | | | Analyses | |
| 8 | cyclopentyl | morpholino | 40 | 152(1) | N | 25.09 | 24.78 |
| | | | | | C | 55.30 | 55.64 |
| | | | | | H | 7.33 | 7.44 |
| | | | | | N | 21.50 | 21.31 |
| | | | | | Cl⁻ | 10.90 | 10.84 |

(1) Hydrochloride: prepared by addition of one equivalent of hydrochloric acid in diethyl ether to one equivalent of the free base dissolved in diethyl ether.

2. 2-Cyclopropylamino-4-methyl-6-(8-oxa-3-azabicyclo[3,2,1]oct-3-yl)-1,3,5-triazine hydrochloride (compound 9).

2 equivalents of triethylamine dissolved in dioxane are added to one equivalent of 8-oxa-3-azabicyclo[3,2,-1]octane hydrochloride suspended in the same solvent.

The 8-oxa-3-azabicyclo[3,2,1]octane used as the starting compound in this example is a known compound; it has been prepared according to the method of F.H. NEWS et al. (J. Chem. Soc., 1948, 115–158). The compounds summarized in Table III are prepared in the same manner.

TABLE III

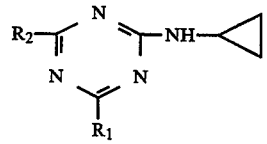

| Compound | R₁ | R₂ | Yield (%) | M.P. (°C.) | | calc. % | found % |
|---|---|---|---|---|---|---|---|
| | | | | | | Analyses | |
| 10 | ethyl | OABCO(2) | 74 | 156–159(1) | C | 53.93 | 53.81 |
| | | | | | H | 7.11 | 7.14 |
| | | | | | N | 22.46 | 22.22 |
| | | | | | Cl⁻ | 11.37 | 11.49 |
| 11 | n-propyl | OABCO | 72 | 129–133(1) | C | 55.29 | 54.97 |
| | | | | | H | 7.42 | 7.40 |
| | | | | | N | 21.49 | 20.98 |
| | | | | | Cl⁻ | 10.88 | 10.86 |
| 12 | isopropyl | OABCO | 59 | 149–153(1) | C | 55.29 | 55.10 |
| | | | | | H | 7.42 | 7.39 |
| | | | | | N | 21.49 | 21.25 |
| | | | | | Cl⁻ | 10.88 | 10.92 |
| 13 | cyclopropyl | 3-HO-1-azetidinyl | 30.4 | 111 | C | 58.30 | 58.42 |
| | | | | | H | 6.88 | 6.84 |
| | | | | | N | 28.34 | 28.20 |
| 14 | cyclopropyl | 3-CH₃O-1-azetidinyl | 47.3 | 64 | C | 59.77 | 60.05 |
| | | | | | H | 7.28 | 7.30 |
| | | | | | N | 26.82 | 26.50 |
| 15 | n-propyl | 3-HO-1-azetidinyl | 46.4 | 76 | C | 57.83 | 57.64 |
| | | | | | H | 7.63 | 7.66 |
| | | | | | N | 28.11 | 27.99 |
| 16 | cyclopropyl | OABCO | 35 | 177 | C | 55.64 | 55.59 |
| | | | | | H | 6.80 | 6.84 |
| | | | | | N | 21.64 | 21.40 |
| 17 | cyclopropyl | 3-oxo-1-azetidinyl | 17.1 | 192–194(1) | C | 51.15 | 50.36 |
| | | | | | H | 5.68 | 5.74 |
| | | | | | N | 24.87 | 24.30 |

(1) Hydrochloride
(2) OABCO = 8-oxa-3-azabicyclo[3,2,1]oct-3-yl 1 equivalent of 2-chloro-4-cyclopropylamino-6-methyl-1,3,5-triazine dissolved in dioxane is then added. The mixture is heated under reflux for some hours. It is cooled to room temperature and the precipitate which has formed is filtered off. The filtrate is evaporated under reduced pressure and the residue is redissolved in dichloromethane. The solution is washed with water. The organic phase is separated off and dried over sodium sulfate, and the solvent is then evaporated under reduced pressure. The residue thus obtained is purified by chromatography on silica (eluent: 98:2 (v/v) dichloromethane-ethanol). 2-cyclopropylamino-4-methyl-6-(8-oxa-3-azabicyclo[3,2,1]oct-3-yl)-1,3,5-triazine hydrochloride is prepared by addition of one equivalent of hydrochloric acid to the free base in diethyl ether. Yield: 63%. M.P.: 220°–223° C.

Analysis for C₁₃H₁₉N₅O.HCl in %: Calc. C 52.44 H 6.77 N 23.52 Cl⁻11.92 found 52.40 6.74 23.43 11.84.

The 3-azetidinone hydrochloride used as the starting compound for the synthesis of compound 17 is known; it has been prepared according to the method of H. BAUMANN et al. (Helv. Chim. Acta, 71, (1988), 1035).

3.
a. 2-Cyclopropyl-4-cyclopropylamino-6-thiomorpholino-1,3,5-triazine (compound 18).

12.2 g of 2-chloro-4-cyclopropyl-6-cyclopropylamino-1,3,5-triazine (0.057 mole), 5.97 g of thiomorpholine (0.057 mole) and 8 g of potassium carbonate (0.057 mole) are mixed in 100 ml of isopropyl alcohol and the mixture is heated at 75°–80° C. for 2 hours. It is cooled, the salts are filtered off and the filtrate is evaporated to dryness. The residue is taken up in 200 ml of dichloromethane, the solution is washed with water and dried over sodium sulfate and the solvent is evaporated. The product obtained is crystallized from a 1:2 (v/v) mixture of ethyl acetate-hexane to give 13.18 g of 2-cyclopropyl-4-cyclopropylamino-6-thiomorpholino-1,3,5-triazine. Yield: 83.5%. M.P.: 133°–134° C.

Analysis for $C_{13}H_{19}N_5S$ in %: calc.: C 56.32, H 6.86, N 25.27, S 11.55, found: 56.06, 6.93, 24.90, 11.40.

The following compounds are prepared in the same manner:

b. 2-Cyclopropyl-4-cyclopropylamino-6-thiomorpholino-1,3,5-triazine S-oxide (compound 19). Yield: 23%. M.P.: 167°–168° C.

Analysis for $C_{13}H_{19}N_5OS$ in %: calc.: C 53.24, H 6.48, N 23.89, S 10.92, found: 53.10, 6.52, 23.46, 10.62.

c. 2-Cyclopropyl-4-cyclopropylamino-6-thiomorpholino-1,3,5-triazine S,S-dioxide (compound 20). Yield: 17%. M.P.: 178°–179° C.

Analysis for $C_{13}H_{19}N_5O_2S$ in %: calc.: C 50.49, H 6.15, N 22.65, S 10.36, found: 50.72, 6.18, 22.56, 10.35.

d. 2-Cyclopropyl-4-cyclopropylamino-6-(3-thiazolidinyl)-1,3,5-triazine (compound 21). Yield: 61.2%. M.P.: 110°–111° C.

Analysis for $C_{12}H_{17}N_5S$ in %: calc.: C 54.75, H 6.46, N 26.61, S 12.17, found: 54.83, 6.46, 26.68, 12.30.

e. 2-Cyclopropyl-4-cyclopropylamino-6-(3-thiazolidinyl)-1,3,5-triazine S,S-dioxide (compound 22). Yield: 35.6%. M.P.: 142°–143° C.

Analysis for $C_{12}H_{17}N_5O_2S$ in %: calc.: C 48.81, H 5.76, N 23.73, S 10.87, found: 49.11, 6.78, 23.69, 10.96.

The thiazolidine 1,1-dioxide hydrochloride used as starting material for the synthesis of compound 22 above has been prepared according to a process in 3 steps:

a. N-tert-butoxycarbonyl-thiazolidine. 24 g (0.11 mole) of di-tert-butyl dicarbonate dissolved in 50 ml of dioxane are added dropwise to a solution of 8.9 g (0.1 mole) of thiazolidine in 50 ml of dioxane and 50 ml of water, while maintaining the pH between 10 and 10.5 by addition of soda lye. The mixture is stirred at room temperature for 6 hours. The formed salts are filtered off and the organic solvent is evaporated under reduced pressure. The aqueous residue is extracted with dichloromethane (2×50 ml), the organic phase is decanted, dried over sodium sulfate and the solvent is evaporated off. The residue is purified by distillation under reduced pressure. 16.3 g of N-tert-butoxycarbonyl-thiazolidine are obtained. Yield: 86.2%. B.P.: 56°–57° C./6.7 mbars.

b. N-tert-butoxycarbonyl-thiazolidine 1,1-dioxide. 30.7 g (0.05 mole) of oxone ($2KHSO_5.KHSO_4.K_2SO_4$) dissolved in 300 ml of water are added dropwise to a solution of 7.3 g (0.0385 mole) of N-tert-butoxycarbonyl-thiazolidine dissolved in 100 ml of dichloromethane and 200 ml of methanol at room temperature. The mixture is stirred at 20° C. for 24 hours, 500 ml of water are then added, the mixture is extracted with dichloromethane (3×200 ml), the organic phase is dried over sodium sulfate and the solvent is evaporated off. The residue crystallizes from 300 ml of isopropyl ether. 6.58 g of N-tert-butoxycarbonyl-thiazolidine 1,1-dioxide are obtained.

Yield: 74.4%. M.P.: 106°–107° C. Analysis for $C_8H_{15}NO_4S$ in %: calc.: C 43.44, H 6.79, N 6.33, S 14.48, found: 43.52, 6.78, 6.33, 14.36.

c. Thiazolidine 1,1-dioxide hydrochloride 1.8 g (0.0081 mole) of N-tert-butoxycarbonyl-thiazolidine 1,1-dioxide and 50 ml of a 2N hydrochloric acid solution in diethyl ether are mixed. The suspension is stirred at 20° C. for 6 hours, then allowed to stand for 48 hours. The white precipitate of thiazolidine 1,1-dioxide hydrochloride is filtered off, washed with diethyl ether and dried. 0.83 g of product is thus obtained.

Yield: 65.3%. M.P.: 173°–174° C. Analysis for $C_3H_7NO_2S.HCl$ in %: calc.: C 22.86, H 5.08, N 8.89, found: 23.29, 5.01, 8.69.

EXAMPLE 3

Preparation of the cyclopropylamino-1,3,5-triazines of the formula I according to process (b).

A. Preparation of the starting chloro-1,3,5-triazines of the formula IV. 2-Chloro-4-cyclopropyl-6-morpholino-1,3,5-triazine. A solution of 2.61 g (0.03 mole) of morpholine in 20 ml of chloroform is added in the course of 30 minutes to a solution of 5.7 g (0.03 mole) of 2,4-dichloro-6-cyclopropyl-1,3,5-triazine in 50 ml of chloroform, cooled to between 3° and 5° C. The temperature of the mixture is allowed to return to about 10° C., then the mixture is cooled again to 5° C. and a solution of 4.14 g (0.03 mole) of potassium carbonate in 15 ml of water is added dropwise. The mixture is then stirred at room temperature for two hours. 30 ml of water are added and the organic phase is separated off. The solution is washed with water and dried over sodium sulfate, and the solvent is evaporated under reduced pressure. The residue is purified by chromatography on silica (eluent: 96.5:3.5 (v/v) dichloromethane-ethylacetate) and then recrystallized from hexane. 5.5 g of 2-chloro-4-cyclopropyl-6-morpholino-1,3,5-triazine are thus obtained.

Yield: 76.2%. M.P.: 99°–100° C. Analysis for $C_{10}H_{13}ClN_4O$ in %: calc.: C 49.89, H 5.41, N 23.28, Cl 14.76, found: 49.91, 5.44, 23.06, 14.46.

B. Preparation of the cyclopropylamino-1,3,5-triazines of the formula I. 2-Cyclopropyl-4-cyclopropylamino-6-morpholino-1,3,5-triazine. 2.85 g (0.050 mole) of cyclopropylamine dissolved in 20 ml of dioxane are added to a solution of 5.1 g (0.021 mole) of 2-chloro-4-cyclopropyl-6-morpholino-1,3,5-triazine in 50 ml of dioxane at room temperature. The mixture is heated under reflux for 5 hours. The solvent is then evaporated under reduced pressure and the residue is dissolved in 50 ml of dichloromethane and 50 ml of water. The organic phase is separated off and dried over sodium sulfate and the solvent is evaporated under reduced pressure. The residue crystallizes from cold hexane. 5.22 g of product are obtained. This product forms a hydrochloride in an ethanol-diethyl ether mixture. 5.1 g of 2-cyclopropyl-4-cyclopropylamino-6-morpholino-1,3,5-triazine hydrochloride, which is identical to compound 3 prepared in example 2.B.1., are obtained.

Yield: 81.7%. M.P.: 183°–184° C. (acetonitrile). Analysis for $C_{13}H_{19}N_5O.HCl$ in %: calc.: C 52.44, H 6.72, N 23.53, Cl$^-$ 11.93, found: 52.46, 6.73, 23.44, 11.89.

EXAMPLE 4

Preparation of the cyclopropylamino-1,3,5-triazines of the formula I according to process (c).

A. N-cyano-N'-cyclopropylguanidine. 9.36 g (0.1 mole) of cyclopropylamine hydrochloride and 8.9 g (0.1 mole) of the sodium salt of cyanoguanidine are suspended in 100 ml of n-butanol and 8 ml of water. The mixture is heated under reflux for 2 hours. The suspension is filtered and the filter cake is washed with 100 ml of n-butanol. The filtrate is evaporated under reduced pressure. The residual oil is taken up in 300 ml of acetonitrile. The mixture is heated to reflux, filtered hot and the filter cake is washed with acetonitrile. The filtrate is evaporated off and the oil obtained crystallizes slowly.

7.7 g of N-cyano-N'-cyclopropylguanidine are obtained.

Yield: 62%. M.P.: 106° C. (isopropyl alcohol/diethyl ether). Analysis for $C_5H_8N_4$ in %: calc.: C 48.37, H 6.49, N 45.13, found: 48.40, 6.50, 45.15.

B. Preparation of the starting N-cyclopropylbiguanides of the formula VI.

1. N-[imino(cyclopropylamino)methyl]-4-morpholinecarboximidamide hydrochloride.

A mixture of 4.0 g (32.3 mmoles) of N-cyano-N'-cyclopropylguanidine and 3.98 g (32.3 mmoles) of morpholine hydrochloride is heated at 160° C. under a nitrogen atmosphere for 2 and a half hours. The solid mass obtained is dissolved in 200 ml of boiling isopropyl alcohol. The mixture is filtered hot and the filtrate is concentrated until a solid suspension appears. The mixture is then cooled to room temperature and 200 ml of diethyl ether are added. The reaction product crystallizes. It is filtered, washed with diethyl ether and dried. 6.8 g of N-[imino(cyclopropylamino)methyl]-4-morpholinecarboximidamide hydrochloride are obtained.

Yield: 85%. M.P.: 195°–196° C. Analysis for $C_9H_{17}N_5O$.HCl in %: calc.: C 43.63, H 7.32, N 28.27, $Cl^-$ 14.21, found: 43.60, 7.35, 27.93, 14.18.

2. N-[imino(cyclopropylamino)methyl]-4-thiomorpholinecarboximidamide S,S-dioxide hydrochloride.

This compound is prepared in the same manner as the previous compound by reacting thiomorpholine 1.1-dioxide hydrochloride (British patent No. 874,519) with N-cyano-N'-cyclopropylguanidine at 160° C. for 6 hours. Yield: 58.4%.

The product obtained, which is 90% pure (chromatography), is used as such in the following reaction.

C. Preparation of the cyclopropylamino-1,3,5-triazines of the formula I.

1. 2-Cyclopropylamino-4-(1-methylcyclopropyl)-6-morpholino-1,3,5-triazine (compound 24).

0.48 g (20 mmoles) of sodium is dissolved in 20 ml of anhydrous ethanol. This solution is added to an ethanol solution containing 2.48 g (10 mmoles) of N-[imino(cyclopropylamino)methyl]-4-morpholinecarboximidamide hydrochloride, and 2.82 g (22 mmoles) of ethyl 1-methylcyclopropane-carboxylate are then also added to the mixture. The mixture is then heated under reflux under nitrogen for 88 hours. It is cooled, the alcohol is evaporated under reduced pressure and the residue is redissolved in 50 ml of water and 200 ml of dichloromethane. The aqueous phase is separated off and the organic phase is washed twice with 50 ml of water and dried over magnesium sulfate. The solvent is evaporated under reduced pressure and the residue is recrystallized from a 1:1 (v/v) mixture of potroleum ether-dichloromethane. 0.49 g of 2-cyclopropylamino-4-(1-methylcyclopyropyl)-6-morpholino-1,3,5-traizine is obtained.

Yield: 17%. M.P.: 94°–95° C. Analysis for $C_{14}H_{21}N_5O$ in %: calc.: C 61.06, H 7.69, N 25.44, found: 61.15, 7.66, 25.55.

The following compounds are prepared in the same manner:

2. 2-Cyclopropylamino-4-(2-methylcyclopropyl)-6-morpholino-1,3,5-triazine hydrochloride (compound 25). Heating period: 62 hours.

Yield: 38.7%. M.P.: 177°–178° C. Analysis for $C_{14}H_{21}N_5O$.HCl in %: calc.: C 53.93, H 7.06, N 22.47, $Cl^-$ 11.40, found: 54.04, 7.14, 22.19, 11.27.

3. 2-Cyclobutyl-4-cyclopropylamino-6-thiomorpholino-1,3,5-triazine S,S-dioxide hydrochloride (compound 26). Heating period: 18 hours.

Yield: 39%. M.P.: 220°–225° C. (dec.). Analysis for $C_{14}H_{21}N_5O_2S$.HCl in %: calc.: C 46.73, H 6.12, N 19.47, S 9.87, $Cl^-$ 8.90, found: 46.24, 6.02, 19.14, 9.78, 8.70.

4. 2-Cyclopropylamino-4-(2-methylcyclopropyl)-6-thiomorpholino-1,3,5-triazine S,S-dioxide (compound 27). Heating period: 27 hours.

Yield: 93.9%. M.P.: 180°–182° C. Analysis for $C_{14}H_{21}N_5O_2S$ in %: calc.: C 52.01, H 6.50, N 21.67, S 9.91, found: 52.00, 6.54, 21.36, 9.89.

5. 2-Cyclopropylamino-4-(2,2-dimethylcyclopropyl)-6-thiomorpholino-1,3,5-triazine S,S-dioxide (compound 28). Heating period: 6 days.

Yield: 40.1%. M.P.: 170°–172° C. Analysis for $C_{15}H_{23}N_5O_2S$ in %: calc.: C 53.41, H 6.82, N 20.77, S 9.50, found: 54.02, 6.86, 20.88, 9.39.

6. 2-Cyclopropylamino-4-(2-n-propylcyclopropyl)-6-thiomorpholino-1,3,5-triazine S,S-dioxide (compound 29). Heating period: 20 hours in an autoclave at 110° C.

Yield: 28.7%. M.P.: 148°–149° C. Analysis for $C_{16}H_{25}N_5O_2S$ in %: calc.: C 54.70, H 7.12, N 19.84, found: 54.71, 7.10, 20.05.

EXAMPLE 5.

Preparation of the cyclopropylamino-1,3,5-triazines of the formula I according to process (d). A. 2-Cyclopropyl-4-cyclopropylamino-6-(3-thiazolidinyl)-1,3,5-triazine S,S-dioxide (compound 22).

A solution of 30.7 g (0.05 mole) of oxone ($2KHSO_5$.$KHSO_4$.$K_2SO_4$) in 75 ml of water is added dropwise to a solution of 6.58 g (0.025 mole) of 2-cyclopropyl-4-cyclopropylamino-6-(3-thiazolidinyl)-1,3,5-triazine (compound 21) in 75 ml of dichloromethane and 150 ml of methanol, at a temperature between 10 and 15° C. The mixture is stirred at room temperature for 3 hours. 3 g of oxone dissolved in 10 ml of water are then added again and stirring is continued for 2 hours. 200 ml of water are added, the mixture is extracted with dichloromethane (3×100 ml), the organic phase is separated off and dried over sodium sulfate and the solvent is evaporated. The residue is purified by chromatography on silica (eluent: 98:2 (v/v) dichloromethane-ethanol).

3 g of 2-cyclopropyl-4-cyclopropylamino-6-(3-thiazolidinyl)-1,3,5-triazine S,S-dioxide identical to the compound prepared in example 2.B.3.e. are obtained.

Yield: 40.7%. M.P.: 142°–143° C. (ethyl acetate-hexane).

B. 2-Cyclopropyl-4-cyclopropylamino-6-(3-thiazolidinyl)-1,3,5-triazine S-oxide (compound 23).

A solution of 15.35 g (0.025 mole) of oxone in 150 ml of water is added dropwise and without exceeding the temperature of 5° C., to a solution of 11.85 g (0.045 mole) of 2-cyclopropyl-4-cyclopropylamino-6-(3-thiazolidinyl)-1,3,5-triazine (compound 21) in 150 ml of dichloromethane and 300 ml of methanol, cooled to about 0° C. The mixture is then further stirred at 5° C. for 30 minutes. The precipitate of mineral salts is filtered off on Hyflo-cel. The organic phase is eliminated by decantation. The aqueous phase is diluted with 400 ml of water and extracted with dichloromethane (2×200 ml). The organic phase is dried over sodium sulfate and the solvent evaporated off. The evaporation residue is taken up in 100 ml of dichloromethane, filtered off and concentrated. A first crop of 2.83 g of a solid product is obtained. The aqueous phase is rendered alkaline and extracted with dichloromethane (3×100 ml), the organic phase is dried over sodium sulfate and the solvent is evaporated. 8.41 g of a solid residue are thus obtained (second crop). The two crops are brought together and purified by chromatography on silica (eluent: 93:3 (v/v) dichloromethane-ethanol). 7.66 g of 2-cyclopropyl-4-cyclopropylamino-6-(3-thiazolidinyl)-1,3,5-triazine S-oxide, crystallized from a 1:3 (v,v) mixture of ethyl acetate-hexane, are obtained.

Yield: 61%. M.P.: 136°–137° C. Analysis for $C_{12}H_{17}N_5OS$ in %: calc.: C 51.61, H 6.09, N 25.03, S 11.47, found: 51.79, 6.10, 25.09, 11.50

As indicated above, the substituted cyclopropylamino-1,3,5-triazines of the formula I and their non-toxic pharmaceutically acceptable acid addition salts have the property of correcting the effects of hypofunctioning of the cholinergic system and consequently have a favorable activity on mnemic processes. In addition, they have a central serotonergic and a bronchospasmolytic activity; they oppose the release of mastocyte mediators, have an anti-inflammatory and anti-edema activity and potentiate the effect of a β-adrenergic agonist on muscle relaxation.

The pharmacological tests described below demonstrate these various advantageous properties.

1. Activity on mnemic processes

The compounds according to the present invention were studied with the aim of demonstrating on the one hand their property of promoting learning, expressed as the reduction in the number of trials needed to achieve a predetermined criterion, and on the other hand their property of counteracting the amnesia caused by administration of scopolamine.

To this end, the method of multiple-trial passive avoidance has been used. This method is well-known for evaluating the effects which a product exerts on the memory and learning (A. FINE et al., Proc. Natl. Acad. Sci. USA, 82, (1985), 5227–5230). The test is carried out on male Sprague-Dawley rats (160–200 g). which are kept in standard cages throughout the experiment. The apparatus used is a transparent square cage with 35 cm sides and 25 cm high, fitted with a grid floor which can be electrified. A rubber insulating mat (10×17 cm) is placed on the floor in one of the corners of the cage.

To evaluate whether a compound can promote learning, the following test is carried out.

Each animal is placed on the rubber mat and the time the animal takes to decide to leave this position to explore the cage is recorded. After 20 seconds of exploration, the animal receives an electric shock (3 seconds duration) in the paws, causing an escape reaction. The rat is immediately removed from the apparatus and replaced in its original cage. This experiment is repeated until the animal remains on the rubber mat for at least 180 seconds in order to avoid the electric shock. The learning is expressed by the average number of trials needed to reach a period of 180 seconds remaining on the mat. A period of remaining on the rubber mat of 180 seconds is regarded as being the maximum performance to be realized by the animal to avoid the electric shock. Rats which remain on the mat for this period have acquired the avoidance reflex and are replaced in their original cage without receiving the electric shock.

To evaluate whether a compound is capable of promoting mnemic retention in the course of time, the following experiment is carried out. Each animal is subjected to four tests at times 0, 4, 24 and 28 hours. In the first test (time 0), the animal is placed on the rubber mat and the time which it takes to decide to leave this position to explore the cage is recorded. After 20 seconds of exploration, the rat receives an electric shock (3 seconds duration) in the paws, causing an escape reaction. The rat is immediately removed from the apparatus and replaced in its original cage. In the course of the three subsequent tests (times: 4, 24 and 28 hours), the animal is replaced on the rubber mat and the time taken to leave this position is recorded. As soon as the four paws of the animal rest on the grid, it receives an electric shock and is removed immediately from the apparatus.

At the start of the experiment, the rats are divided into 4 homogeneous groups of 15 animals. Thirty minutes before each test, each group of animals is subjected to a predetermined treatment:

group 1 receives an intraperitoneal injection of physiological salt solution;

group 2 receives an intraperitoneal injection of the compound to be tested;

group 3 receives an intraperitoneal injection of 0.5 mg of scopolamine and group 4 receives an intraperitoneal injection of 0.5 mg of scopolamine and, simultaneously, an intraperitoneal injection of the compound to be tested.

Groups 1 and 2 are used in the first experiment (learning) and groups 3 and 4 in the second experiment (mnemic retention). The results obtained in this test with the compounds according to the invention are summarized in Table IV. This Table shows the compound subjected to the test (column 1) and the dose administered intraperitoneally, expressed in mg/kg (column 2).

The results obtained in the test used to evaluate learning are given in columns 3 and 4. The figures indicate the average number of trials needed for a control animal (group 1) or an animal treated with the compound (group 2) to learn to remain on the rubber mat for 180 seconds in order to avoid the electric shock. The results were analyzed by the Student test.

The results obtained in the experiment used to evaluate mnemic retention are given in columns 5 to 12. In columns 5 to 8, the figures represent the average periods of remaining on the mat observed respectively at times 0, 4, 24 and 28 hours for the animals of the group 3, treated only with scopolamine, and in columns 9 to 12 the corresponding figures are found for the animals of group 4, treated simultaneously with scopolamine and with the compound tested (at the dose shown in the second column). The favorable influence of a compound in counteracting amnesia induced by scopolamine is demonstrated by the increase in the period of remaining on the mat at each observation. The differences found are analyzed statistically by the Mann-Whitney method.

TABLE IV

| Compound | Dose (mg/kg) | Learning average number of trials | | Mnemic Retention Period of remaining on the mat (in seconds) | | | | | | | |
| | | | | group 3 | | | | group 4 | | | |
| | | group 1 | group 2 | 0 | 4 | 24 | 28 | 0 | 4 | 24 | 28 |
| 1 | 3.0 | 3.7 | 1.4 | 3.7 | 18.1 | 19.7 | 34.3 | 19.2 | 42.8 | 77.2 | 114.6 |

TABLE IV-continued

| Compound | Dose (mg/kg) | Learning average number of trials | | Mnemic Retention Period of remaining on the mat (in seconds) | | | | | | | |
|---|---|---|---|---|---|---|---|---|---|---|---|
| | | | | group 3 | | | | group 4 | | | |
| | | group 1 | group 2 | 0 | 4 | 24 | 28 | 0 | 4 | 24 | 28 |
| 2 | 1.0 | 3.2 | 2.7 | 5.3 | 7.3 | 11.2 | 14.5 | 7.9 | 18.9 | 24.3 | 36.5 |
| 3 | 1.0 | 3.0 | 1.9 | 5.6 | 6.7 | 20.7 | 17.5 | 6.5 | 35.5 | 105.0 | 121.0 |
| 4 | 2.8 | 3.9 | 1.9 | 4.5 | 13.1 | 20.9 | 61.3 | 12.3 | 44.5 | 91.5 | 106.6 |
| 5 | 2.8 | 3.3 | 2.3 | 5.1 | 7.9 | 8.6 | 21.0 | 14.5 | 34.2 | 35.9 | 73.3 |
| 6 | 3.2 | 3.4 | 2.5 | 3.1 | 5.5 | 6.4 | 12.1 | 5.3 | 11.7 | 24.8 | 28.7 |
| 7 | 2.8 | 2.0 | 1.9 | 3.7 | 18.5 | 38.5 | 59.6 | 9.8 | 34.5 | 94.0 | 133.0 |
| 9 | 3.0 | 2.8 | 2.9 | 5.2 | 4.7 | 25.4 | 69.6 | 3.6 | 17.3 | 38.1 | 65.2 |
| 10 | 3.1 | 2.7 | 1.4 | 2.7 | 24.1 | 27.6 | 52.3 | 5.7 | 20.3 | 78.9 | 142.0 |
| 11 | 3.3 | 3.1 | 1.8 | 4.2 | 7.3 | 5.3 | 10.3 | 10.7 | 21.4 | 58.6 | 93.2 |
| 12 | 1.0 | 2.6 | 1.7 | 3.2 | 20.9 | 40.6 | 41.1 | 3.6 | 18.0 | 51.1 | 94.5 |
| 13 | 2.5 | 2.3 | 2.1 | 5.0 | 8.9 | 19.7 | 34.9 | 7.7 | 55.3 | 92.5 | 99.0 |
| 14 | 2.6 | 2.3 | 1.5 | 5.3 | 7.1 | 21.3 | 67.7 | 11.7 | 36.3 | 73.9 | 139.1 |
| 15 | 2.5 | 2.3 | 1.9 | 5.1 | 12.1 | 22.7 | 59.7 | 9.8 | 19.5 | 94.3 | 112.7 |
| 16 | 3.25 | 2.5 | 2.2 | 6.2 | 10.3 | 29.1 | 34.3 | 11.3 | 35.1 | 118.5 | 101.1 |
| physostigmine | 0.4 | 2.6 | 2.3 | 1.7 | 1.4 | 6.9 | 21.3 | 1.9 | 17.8 | 56.2 | 53.4 |

From this Table, it can be seen that:

the compounds according to the invention promote learning of the avoidance reflex: the average number of trials needed to reach the predetermined criterion (maximum period of remaining on the mat of 180 seconds) is lower for the treated animals (column 4) than for the control animals (column 3);

the amnesic effect of scopolamine is very pronounced: it can be seen that the period of remaining on the mat for the animals of group 3 (columns 5 to 8) are clearly less than the 180 seconds realized by the controls after an average number of trials (column 3); and, under these conditions, the favorable influence of the compounds according to the invention in counteracting the amnesic effect of scopolamine is very clear: the animals of group 4, treated simultaneously with scopolamine and with a compound according to the invention, have periods of remaining on the mat, at each observation, which are considerably longer than those for the animals of group 3, treated with scopolamine alone (compare the results of column 5 with those of column 9, 6 with 10, and so on).

physostigmine exerts a favorable action against the amnesic effect of scopolamine, similar to that of the compounds according to the invention, but at a dose which has side effects and is very close to the toxic dose, which is not the case for the compounds according to the invention.

2. Serotonergic activity

A decrease in serotonergic activity has been correlated with the occurrence of affective disorders, such as depression and anxiety. Injection of rats with serotonin or 5-hydroxytryptophan (5-HTP), a serotonin agonist, induces paroxysmal shakes of the head, neck and trunk in this animal, similar to the shuddering of a wet dog shaking itself. This behavior is called "wet dog shake" (WDS) and is used as a model to demonstrate the aminergic and in particular serotonergic properties found in antidepressants (P. BEDARD and C. J. PYCOCK, Neuropharmacology, 16, (1977), 663–670).

The test is carried out in the morning on male Sprague-Dawley rats (±180 g), divided the previous day into groups of 8 animals in residence cages. The cage used for the tests is a transparent enclosure of 12×24×30 cm in height, the floor of which is covered with a layer of sand.

The compounds to be tested, dissolved either in physiological salt solution or in a citrate buffer of pH 5, are administered intraperitoneally in a different dose for each group treated. The control groups receive an intraperitoneal injection of the same vehicle (either physiological salt solution or citrate buffer). After administration of the compound, the animals are immediately placed in the test cage in groups of four at a time, and after a habituation period of 10 minutes, the number of shakes (WDS) which occur over a period of 30 minutes is counted.

The mean values of the results are calculated and analyzed statistically by the Mann-Whitney method.

The mean values of the number of shakes obtained for the compounds according to the invention administered intraperitoneally at the doses indicated (in mg/kg) are given in Table V below.

TABLE V

| | "Wet dog shake" behavior | |
|---|---|---|
| Compound | Dose (mg/kg) | Average number of shakes |
| 1 | 1.0 | 7.8 ± 1.6 |
| 2 | 1.0 | 10.0 ± 3.5 |
| 3 | 0.3 | 5.1 ± 1.0 |
| | 1.0 | 11.9 ± 2.7 |
| 4 | 2.8 | 10.6 ± 4.3 |
| 5 | 2.8 | 8.4 ± 1.6 |
| 6 | 1.0 | 1.9 ± 0.5 |
| | 3.2 | 3.6 ± 1.1 |
| 7 | 2.8 | 7.9 ± 1.8 |
| 10 | 3.1 | 16.3 ± 3.8 |
| 11 | 1.1 | 4.3 ± 1.4 |
| 12 | 3.2 | 16.3 ± 4.2 |
| 13 | 2.5 | 5.6 ± 1.8 |
| 14 | 0.8 | 2.1 ± 0.7 |
| 16 | 1.0 | 10.6 ± 1.8 |
| 17 | 2.8 | 10.5 ± 2.9 |
| 18 | 0.88 | 10.6 ± 3.0 |
| 19 | 0.94 | 16.0 ± 4.7 |
| 20 | 0.99 | 13.6 ± 2.3 |
| 21 | 2.63 | 5.5 ± 2.0 |
| 22 | 0.95 | 8.1 ± 1.7 |
| 23 | 0.89 | 10.1 ± 3.0 |
| 24 | 2.75 | 6.1 ± 2.3 |
| 25 | 1.0 | 19.6 ± 5.0 |
| 26 | 1.15 | 11.8 ± 4.3 |
| 5-HTP/carbidopa (1) | 100.0 | 4.7 ± 1.5 |
| | 200.0 | 19.6 ± 3.0 |

(1) The animals are pretreated with the peripheral decarboxylase inhibitor α-methyldopahydrazine or carbidopa (25 mg/kg, i.p., 30 minutes before the 5-HTP); the measurements are made 90 to 120 minutes after the intraperitoneal injection of 5-HTP.

This Table shows that the compounds according to the invention induce a "wet dog shake" behavior in rats comparable to that caused by injections of a serotonergic agonist such as 5-HTP in the presence of carbidopa, but at doses which are clearly lower.

3. Bronchospasmolytic activity

This activity was measured in the Dunkin-Hartley guinea-pig by the method of H. KONZETT and R. ROESSLER (Naunyn Schmiedebergs Arch. exp. Path. Pharmacol., 195, (1940), 71–74) and compared with that of theophylline.

The anesthetized (urethane) and curarized (gallamine) guinea-pig is placed under assisted respiration. The endotracheal pressure is recorded. Repeated bronchial spasms are induced by successive intravenous injections (every 5 minutes) of serotonin, histamine or acetylcholine, respectively, at a dose which is capable of inducing an increase of the endotracheal pressure of 20 to 50 cm water. The compound to be tested is also administered intravenously two minutes before the administration of the spasmogen and then in 3 to 4 cumulative doses in increasing amounts at intervals of 15 minutes. Six animals per compound to be tested and per spasmogen are used. Table VI below shows the doses of the compounds (ID50 in μmole/kg) which inhibit by 50%, on average over all the animals, the bronchospasms induced.

TABLE VI

| Bronchospasmolytic Activity | | | |
|---|---|---|---|
| | Doses (ID50 in μmole/kg) | | |
| Compound | Serotonin | Histamine | Acetylcholine |
| 1 | 0.01 | 0.01 | 0.1 |
| 2 | 0.5 | 0.3 | 0.5 |
| 3 | 0.1 | 0.03 | 0.07 |
| 4 | 0.03 | 0.004 | 0.03 |
| 5 | 0.1 | 0.06 | 0.1 |
| 6 | 0.1 | 0.1 | 0.3 |
| 7 | 0.4 | 0.2 | 0.7 |
| 8 | 0.3 | 0.1 | 0.2 |
| 9 | 1.0 | 0.4 | 2.1 |
| 10 | 0.3 | 0.1 | 0.5 |
| 11 | 0.1 | 0.1 | 0.09 |
| 12 | 0.06 | 0.04 | 0.2 |
| 13 | 0.6 | 0.1 | 1.3 |
| 14 | 0.2 | 0.09 | 0.5 |
| 15 | 0.2 | 0.08 | 0.3 |
| 16 | 0.009 | 0.009 | 0.05 |
| 17 | 0.2 | 0.1 | 0.2 |
| 18 | — | 0.003 | — |
| 19 | 0.04 | 0.02 | 0.1 |
| 20 | 0.4 | 0.03 | 0.1 |
| 24 | — | 0.04 | — |
| 26 | — | 0.03 | — |
| theophylline | 4.6 | 5.6 | 10.0 |

It can be seen from this Table that the compounds according to the invention have a remarkable bronchospasmolytic activity with respect to bronchospasms induced by, respectively, serotonin, histamine or acetylcholine.

4. Anti-inflammatory and anti-edema activity

The reaction between a soluble antigen and antibodies in the organism may lead to an acute inflammatory reaction accompanied by release of histamine, modification of vascular permeability and formation of a localized edema. The purpose of the "reverse passive Arthus" (RPA) test is to demonstrate the anti-inflammatory properties of a compound on the plantar edema induced experimentally by immune complexes in the Sprague-Dawley rat (P. J. BAILEY and A. STURM, Biochem. Pharmacol., 32, (1983), 475). To this end, the Arthus reaction is induced by subplantar administration of 0.1 ml of heterologous antivalbumin reaginic serum into the right hind paw and by simultaneous intravenous injection of 1 ml/kg ovalbumin (25 mg/ml). The compound to be tested is administered intravenously 30 seconds before induction of the Arthus reaction, in a least 3 different doses. A group of 6 rats is used per dose of compound to be tested. The volume of the paw is measured by plethysmometry before the Arthus reaction and 3 to 5 hours after induction of the Arthus reaction, both in the control animals and in the treated animals. The effect of a compound on the reduction in the edema for each dose and at each measurement time (3 hours and 5 hours) is expressed in % of the edema observed in the control animals.

The doses of the compounds (ID30 in μmole/kg) which inhibit by 30%, on average over all the animals, the volume of the edema observed in the control animals are given in Table VII below.

TABLE VII

| Anti-inflammatory and anti-edema activity | | |
|---|---|---|
| | Dose (ID30 in μmole/kg) | |
| Compound | 3 hours | 5 hours |
| 1 | 2.0 | 2.0 |
| 2 | 2.3 | 0.7 |
| 3 | 0.8 | 0.4 |
| 4 | 9.0 | 10.0 |
| 5 | 3.1 | 27.0 |
| 6 | 12.0 | 9.0 |
| 7 | 7.7 | 11.0 |
| 8 | 4.0 | 4.0 |
| 9 | 3.4 | 4.4 |
| 11 | 0.5 | 0.4 |
| 12 | 2.5 | 3.0 |
| 13 | 9.0 | 4.0 |
| 14 | 16.0 | 12.0 |
| 15 | 39.0 | 4.0 |
| 16 | 1.5 | 2.0 |
| 17 | 1.0 | 1.0 |
| 18 | 1.0 | 1.0 |
| 19 | 0.02 | 0.02 |
| 20 | 1.0 | 0.5 |
| theophylline | 18.0 | 10.0 |

This Table shows that the compounds according to the invention have an anti-inflammatory and anti-edema activity which is clearly superior to that of theophylline.

5. Inhibition of the anaphylactic release of histamine

The test has two purposes: on the one hand to evaluate the "in vitro" inhibitory activity of a compound on the anaphylactic release of histamine caused by degranulation of mastocytes in the guinea-pig lungs, and on the other hand to demonstrate a possible potentiation effect (synergism) on the inhibitory activity of a β-adrenergic agonist, for example isoprenaline, on this same release of histamine (E. S. K. ASSEM and H. O. SCHILD, Int. Arch. Allergy, 40, (1971), 576–589).

Dunkin-Hartley guinea-pigs which are first passively sensitized by an intravenous injection of 1 ml of isologous antiovalbumin serum are used.

Twenty-four hours after the injection, the lungs are then perfused with a Tyrode buffer to evacuate the blood, and then removed and cut into sections of 1 mm. These sections are divided up into test tubes (3 sections per tube) to give 10 experimental groups of lung sections per guinea-pig.

A "positive" control group of lung sections is stimulated by addition of an ovalbumin solution (0.1 mg/ml) to induce the anaphylactic release of histamine and serves to determine the maximum amount of histamine (100%) which can be released. A "negative" control group which is not stimulated by ovalbumin serves to determine the naturally released amount of histamine (spontaneous release).

In three other groups, the lung sections are incubated at 37° C. for 30 minutes in the ovalbumin solution in the presence of three different doses of the compound to be tested (one dose per group). To detect a potentiation effect of a compound according to the invention on the inhibition of histamine release by isoprenaline, three other groups of lung sections are treated in the same manner as above, but the incubation medium also contains isoprenaline at a dose of $10^{-7}$ mole per liter. At this dose, isoprenaline inhibits the release of histamine by 30 to 40%, which is verified on a control group treated only with isoprenaline alone at this dose. In addition, a supplementary control group which is not stimulated by ovalbumin is used to detect a possible spontaneous release of histamine by the highest dose of the compound tested. In each group, the histamine released in the incubation medium is measured by spectrofluorometry (D. P. EVANS et al., Life Sci., 12, (1973), 327–336).

The results obtained enable a minimum inhibitory dose (MID) (proper effect) to be determined for each compound, that is to say the dose of the compound at which the amount of histamine released is lower than that of the "positive" control group and at which this difference is statistically significant, and a minimum potentiating dose (MPD), which is the dose of compound which induces an inhibition greater than that of isoprenaline at a dose of $10^{-7}$ mole per liter. The minimum inhibitory doses (MID) and the minimum potentiating doses (MPD), expressed in μmole/l, obtained in this test with the compounds according to the invention and with theophylline as the reference substance are given in Table VIII below.

TABLE VIII

Inhibition of the anaphylactic release of histamine

| Compound | Minimum inhibitory dose (in μmole/l) | Minimum potentiating dose (in μmole/l) |
| --- | --- | --- |
| 1 | 0.1 | 0.32 |
| 2 | 1.0 | 3.2 |
| 3 | 0.032 | 0.32 |
| 4 | 0.32 | 0.1 |
| 5 | 0.32 | 3.2 |
| 6 | 1.0 | 1.0 |
| 7 | 0.32 | 1.0 |
| 8 | 1.0 | 10.0 |
| 9 | 3.2 | 3.2 |
| 10 | 3.2 | 0.32 |
| 11 | 1.0 | 0.32 |
| 12 | 0.1 | 0.1 |
| 13 | 1.0 | 1.0 |
| 14 | 1.0 | 0.32 |
| 15 | 10.0 | 3.2 |
| 16 | 0.1 | 0.032 |
| 17 | 3.2 | 1.0 |
| 18 | 0.1 | 1.0 |
| 19 | 1.0 | 0.1 |
| 20 | 1.0 | 0.32 |
| 21 | 0.1 | 0.32 |
| 22 | 0.1 | 0.032 |
| 24 | 0.032 | 0.32 |
| 25 | 0.032 | 0.032 |
| 26 | 1 | 0.32 |
| theophylline | 100.0 | 1000.0 |

It can be seen from this Table that the compounds according to the invention are much more active than theophylline in inhibiting the anaphylactic release of histamine (proper effect) and at the same time have, at low doses, a potentiating effect on the inhibiting effect of isoprenaline obtained at a dose of $10^{-7}$ mole/liter.

6. Potentiation of the myorelaxing effect of isoprenaline on the ileum of the guinea-pig (cf. R. A. TURNER, "Screening Methods in Pharmacology", Ed. Acad. Press, San Diego, 1965, chapter IV, pages 43–47). Fragments of the longitudinal muscles of the ileum of Dunkin-Hartley guinea-pigs (250 to 500 g) attached to an isometric force indicator are dipped in a Tyrode solution (37°±1° C., pH 7.6; 5.6 mmoles/l of glucose), oxygenated by passing a stream of gas (mixture of 95% $O_2$–5% $CO_2$) and tightened with a force of 1 g. After stabilization of the tension, successive cycles of histamine injection (histamine dihydrochloride at a dose of 3.2 μmoles/l) are effected by means of a perfusion pump of the Braun type. Each injection cycle comprises the 6 following successive phases: a rest phase (duration: 25 seconds), a histamine injection phase (duration: 6 seconds), a period of muscular contraction (duration: 24 seconds), a first wash with water (duration: 25 seconds), a period of stabilization, during which the muscle returns to the starting tension (duration: 35 seconds), followed by a second wash with water (duration: 25 seconds).

Inhibition cycle: When the successive contractions induced by the histamine injections have become reproducible, the compound to be tested is injected immediately after the second wash. The contraction induced by the following injection of histamine is measured and compared with the average of the three preceding contractions caused by the repeated injections of histamine (control contractions). From the result obtained, the percentage inhibition of the contraction is calculated. Several cycles of histamine injection are then performed again, until the contractions of the muscle become reproducible again; the muscle is then ready for testing of another compound. The potentiating effect of a compound is measured in the course of a so-called "potentiation" cycle, which comprises three successive inhibition cycles. In the first inhibition cycle, the percentage inhibition of the contraction obtained by injection of isoprenaline alone at a dose of $10^{-7}$ mole/l is determined. At this dose, the percentage inhibition of the contraction is usually between 10 and 25%. In the course of the second inhibition cycle, the percentage inhibition of the contraction obtained with the compound to be tested, injected alone at a given dose, is determined. In the third inhibition cycle, isoprenaline and the compound to be tested are injected simultaneously, and the percentage inhibition of the contraction is calculated for the dose used of the compound tested.

The same experiments are repeated for each of the doses of the compounds tested.

From the results obtained, the minimum potentiating dose (MPD) is determined for each compound tested; this dose corresponds to the dose of compound at which the inhibition obtained with the mixture of compound and isoprenaline is significantly superior ($p<0.05$) to the sum of each of the inhibitions obtained when the compound and isoprenaline are injected alone. In Table IX below, the minimum dose, expressed in μmole/l, which potentiates the myorelaxing effect of isoprenaline administered at a dose of $10^{-7}$ mole/l, is given for the compounds according to the invention in comparison with theophylline.

TABLE IX

Potentiation of the myorelaxing effect of isoprenaline on the ileum of the guinea-pig

| Compound | Minimum potentiating dose (in μmole/l) |
|---|---|
| 1 | 0.032 |
| 2 | 1.0 |
| 3 | 0.032 |
| 4 | 0.032 |
| 5 | 1.0 |
| 6 | 1.0 |
| 7 | 0.32 |
| 9 | 10.0 |
| 10 | 1.0 |
| 11 | 0.032 |
| 12 | 0.01 |
| 13 | 1.0 |
| 14 | 1.0 |
| 15 | 3.2 |
| 16 | 0.032 |
| 17 | 0.32 |
| 18 | 0.1 |
| 19 | 0.32 |
| 20 | 0.1 |
| theophylline | 1000.0 |

This Table shows that the compounds according to the invention are much more active than theophylline in potentiating the myorelaxing effect of isoprenaline.

7. Effect on polymorphonuclear neutrophil granulocytes

Polymorphonuclear neutrophil granulocytes (PMN) are cells which are mobilized during inflammatory phenomena and which can be stimulated by various compounds, such as, for example, formylmethionyl-leucyl-phenylalanine (FMLP) or prostaglandins E (PGE$_1$). The PMN granulocytes respond to these extracellular stimuli with an activation of the oxygen metabolism with release of toxic oxygenated metabolites. An excessive response of the PMN granulocytes may be the cause of a painful inflammation and is also accompanied by a reduction in the level of cyclic adenosine monophosphate (cAMP) in these granulocytes. Consequently, compounds which inhibit the respiratory burst of PMN granulocytes or which increase the level of cAMP can be regarded as very important in the treatment of arthritis and asthma. The aim of the pharmacological test described below is to show that the compounds according to the invention have a double character: on the one hand, they inhibit the stimulation of PMN granulocytes, and on the other hand, they increase the level of cAMP in these cells.

Inhibition of the stimulation of PMN granulocytes

The stimulation of PMN granulocytes is evidenced by the chemiluminescence which accompanies the activation of the oxygen metabolism when these cells are stimulated in the presence of luminol (5-amino-2,3-dihydro-1,4-phthalazinedione).

Rat PMN granulocytes ($5 \times 10^6$/ml) are preincubated in a phosphate buffer (150 μmoles/liter, pH 7.4), containing luminol at a concentration of $10^{-5}$ mole per liter, for 15 minutes at 37° C. and then for 5 minutes in the presence of the compound to be treated at a concentration of $10^{-6}$ mole/liter.

The reaction of stimulation of PMN granulocytes is initiated by the addition of FMLP to the medium at a final concentration of $3.2 \times 10^{-7}$ mole/liter. The luminescence which results from the stimulation is measured by means of an LKB 1251 luminometer according to the method of C. DAHLGREN and O. STENDAHL (Infection and Immunology, 37, (1982), 34–39). An experimental cycle lasts 38 seconds. The reaction is repeated 9 times for each compound to be tested and the average of the results obtained is calculated. In Table X below, the mean percentage of residual chemiluminescence calculated with respect to a control test, in the course of which the PMN granulocytes are incubated and stimulated by FMLP in the absence of the compound to be tested (100% chemiluminescence), is given for the compounds according to the invention and for theophylline (reference compound).

TABLE X

Inhibition of the stimulation of PMN granulocytes

| Compound ($10^{-6}$ mole/l) | Residual chemiluminescence (in %) |
|---|---|
| 1 | 47 |
| 2 | 68 |
| 3 | 39 |
| 4 | 45 |
| 5 | 74 |
| 6 | 55 |
| 7 | 54 |
| 9 | 82 |
| 10 | 56 |
| 11 | 44 |
| 12 | 36 |
| 13 | 79 |
| 14 | 51 |
| 15 | 70 |
| 16 | 42 |
| theophylline | 100 |

This Table shows that at the concentration of $10^{-6}$ mole/l at which all the compounds according to the invention are tested, theophylline is completely inactive. In contrast, it can be seen that at this concentration, the compounds according to the invention cause a significant reduction in the chemiluminescence and thus induce a significant inhibition of the stimulation of PMN granulocytes.

It has also been observed that a concentration 100 times higher ($10^{-4}$ mole/l) is needed to obtain a comparable effect with theophylline (residual chemiluminescence of 65%).

Increase in the level of cAMP

Rat PMN granulocytes ($10^7$ in 200 μl) are incubated in a phosphate buffer (150 μmoles/liter, pH 7.4) at 37° C. for 3 minutes in the presence of the compound to be tested at a concentration of $3.2 \times 10^{-6}$ mole per liter, and of PGE$_1$ in a concentration of $10^{-6}$ mole/liter. The reaction is then stopped by addition of 1 ml of propanol. After centrifugation at 15,000 g for 3 minutes, the supernatant is recovered and evaporated and the amount of cAMP in the residue is determined by radioimmunological assay according to the process recommended by the supplier of the reagent used for this purpose (Amersham).

A control test is carried out under the same conditions, but in the absence of the compound to be tested. The amounts of cAMP (expressed in picomoles) obtained in the course of these tests, in comparison with theophylline, which is also used at a concentration of $3.2 \times 10^{-6}$ mole/liter, are given in Table XI below.

TABLE XI

| Compound | Amount of cAMP produced (in picomoles per $10^7$ cells) |
|---|---|
| 1 | 21.0 |
| 3 | 23.2 |
| 4 | 17.7 |
| 5 | 11.6 |
| 6 | 14.6 |

TABLE XI-continued

| Compound | Amount of cAMP produced (in picomoles per $10^7$ cells) |
|---|---|
| 7 | 15.8 |
| 11 | 16.2 |
| 12 | 16.8 |
| theophylline | 5.0 |
| control | 4.3 |

This Table shows that the compounds according to the invention are more active than theophylline and considerably increase the level of cAMP in PMN granulocytes stimulated by $PGE_1$.

8. Toxicity

The toxicity of the compounds according to the invention has been determined on male NMRI mice by means of the Irwin's test (S. IRWIN, Psychopharmacologia, 13, (1968), 222–257). Progressive doses of the compound to be tested are administered intraperitoneally to groups of three mice until the lethal dose is reached (dose which causes the death of two animals out of three within 48 hours). The lethal dose observed for the compounds according to the invention is given in Table XII below. This Table shows that the compounds according to the invention have a very low toxicity, in contrast to phsostigmine.

TABLE XII

| Compound | Lethal dose (in mg/kg) |
|---|---|
| 1 | 898 |
| 2 | 285 |
| 3 | 297.8 |
| 4 | 165 |
| 5 | 277.4 |
| 6 | 635.6 |
| 7 | 279.3 |
| 8 | 326 |
| 9 | 297.8 |
| 10 | 311.8 |
| 11 | 325.8 |
| 12 | 325.8 |
| 13 | 247.3 |
| 14 | 156.8 |
| 15 | >498 |
| 16 | 194 |
| 17 | 281.5 |
| 18 | 277 |
| 19 | 175.6 |
| 20 | 185 |
| 21 | 263 |
| 22 | 295 |
| 23 | 156 |
| 24 | 825 |
| 25 | 99.7 |
| 26 | 201.5 |
| physostigmine | 0.82 |

9. Posology and administration

The pharmaceutical compositions containing the compounds according to the invention can be administered orally, parenterally or rectally. The pharmaceutical compositions which can be used for oral administration may be solid or liquid, for example in the form of tablets (coated or non-coated), pills, dragees, gelatine capsules, solutions, syrups and the like. The compositions which can be used for parenteral administration are the pharmaceutical forms known for this mode of administration, for example aqueous or oily solutions, suspensions or emulsions.

For rectal administration, the compositions containing the compounds according to the invention are generally in the form of suppositories.

The pharmaceutical forms, such as injectable solutions, injectable suspensions, tablets, drops, suppositories and the like, are prepared by the methods currently used by pharmacists. The pharmaceutical forms also comprise compositions which can deliver the active product in a progressive manner. The compounds according to the invention are mixed with a solid or liquid, nontoxic pharmaceutically acceptable carrier, and optionally with a dispersing agent, a disintegrating agent, a stabilizing agent and the like. Sweetening agents, coloring agents and the like may also be added, if appropriate. The percentage of active compound in the pharmaceutical compositions can vary within very wide limits, according to the patient and the mode of administration, in particular according to the frequency of administration. As regards the daily dosage, this can vary within a wide range of dosage units, for example from 0.05 to active compound, depending upon the mode of administration. Thus, for example, it can be from 0.1 to 0.5 g, preferably 0.1 g, one to several times per day, if the compound is administered in the form of a tablet.

A formulation for tablets is given below as a non-limiting example of a composition containing a compound of the formula I, which can be administered orally:

| | |
|---|---|
| Compound 1 | 50 mg |
| Methylcellulose (Methocel K4M) | 200 mg |
| Dry lactose | 154 mg |
| Aerosil | 5 mg |
| Anhydrous citric acid | 60 mg |
| Talc | 11 mg |
| Magnesium stearate | 20 mg |

We claim

1. A pharmaceutical composition comprising a therapeutically effective amount of a cyclopropylamino-1,3,5-triazine, its optically active isomers or racemic mixtures thereof of the formula

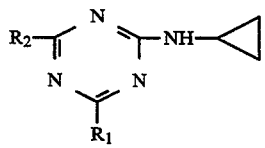

wherein $R_1$ represents an alkyl radical, an unsubstituted cycloalkyl radical or a cycloalkyl radical substituted by at least one alkyl radical, the alkyl radicals having 1 to 3 carbon atoms and the cycloalkyl radicals having 3 to 5 carbon atoms, and $R_2$ represents a bis(2-hydroxyethyl)amino, 3-hydroxy-1-azetidinyl, 3-methoxy-1-azetidinyl, 3-oxo-1-azetidinyl, morpholino, 4-hydroxypiperidino, thiomorpholino, thiomorpholino S-oxide, thiomorpholino S,S-dioxide, 3-thiazolidinyl, 3-thiazolidinyl S-oxide, 3-thiazolidinyl S,S-dioxide or 8-oxa-3-azabicyclo[3,2,1]oct-3-yl radical, or a non-toxic pharmaceutically acceptable acid addition salt thereof, and a pharmaceutically acceptable solid or liquid diluent or carrier therefor.

2. A pharmaceutical composition as claimed in claim 1 wherein the cyclopropylamino-1,3,5-triazine is 2-cyclopropylamino-4-morpholino-6-n-propyl-1,3,5-triazine or a non-toxic pharmaceutically acceptable acid addition salt thereof.

3. A pharmaceutical composition as claimed in claim 1 wherein the cyclopropylamino-1,3,5-triazine is 2-cyclopropyl-4-cyclopropylamino-6-morpholino-1,3,5-triazine or a non-toxic pharmaceutically acceptable acid addition salt thereof.

4. A pharmaceutical composition as claimed in claim 1 wherein the cyclopropylamino-1,3,5-triazine is 2-cyclobutyl-4-cyclopropylamino-6-morpholino-1,3,5-triazine or a non-toxic pharmaceutically acceptable acid addition salt thereof.

5. A pharmaceutical composition as claimed in claim 1 wherein the cyclopropylamino-1,3,5-triazine is 2-cyclopropyl-4-cyclopropylamino-6-thiomorpholino-1,3,5-triazine, or a non-toxic pharmaceutically acceptable acid addition salt thereof.

6. A pharmaceutical composition as claimed in claim 1 wherein the cyclopropylamino-1,3,5-triazine is 2-cyclopropyl-4-cyclopropylamino-6-thiomorpholino-1,3,5-triazine S,S-dioxide or a non-toxic pharmaceutically acceptable acid addition salt thereof.

7. A method for the treatment of inflammation or asthma in a patient in need thereof, which comprises administering to said patient an effective amount of a cyclopropylamino-1,3,5-triazine, its optically active isomers or a racemic mixture thereof of the formula

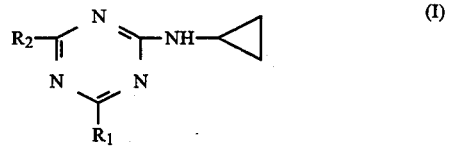

wherein
$R_1$ represents an alkyl radical, an unsubstituted cycloalkyl radical or a cycloalkyl radical substituted by at least one alkyl radical, the alkyl radicals having 1 to 3 carbon atoms and the cycloalkyl radicals having 3 to 5 carbon atoms, and
$R_2$ represents a bis(2-hydroxyethyl)amino, 3-hydroxy-1-azetidinyl, 3-methoxy-1-azetidinyl, 3-oxo-1-azetidinyl, morpholino, 4-hydroxypiperidino, thiomorpholino, thiomorpholino S-oxide, thiomorpholino S,S-dioxide, 3-thiazolidinyl, 3-thiazolidinyl S-oxide, 3-thiazolidinyl S,S-dioxide or 8-oxa-3-azabicyclo[3,2,1]oct-3-yl radical,
or a non-toxic pharmaceutically acceptable acid addition salt thereof.

* * * * *